(12) United States Patent
Mishkin

(10) Patent No.: US 8,883,008 B2
(45) Date of Patent: Nov. 11, 2014

(54) DOUBLE FIBER BUNDLE DIALYZER

(75) Inventor: Gary Mishkin, Potomac, MD (US)

(73) Assignee: Mirimedical, LLC, Potomac, MD (US)

( * ) Notice: Subject to any disclaimer, the term of this patent is extended or adjusted under 35 U.S.C. 154(b) by 427 days.

(21) Appl. No.: 13/054,306

(22) PCT Filed: Jul. 14, 2009

(86) PCT No.: PCT/US2009/050494
§ 371 (c)(1),
(2), (4) Date: Jan. 14, 2011

(87) PCT Pub. No.: WO2010/009095
PCT Pub. Date: Jan. 21, 2010

(65) Prior Publication Data
US 2011/0120930 A1 May 26, 2011

Related U.S. Application Data

(60) Provisional application No. 61/080,769, filed on Jul. 15, 2008.

(51) Int. Cl.
A61M 1/16 (2006.01)
B01D 61/28 (2006.01)
A61M 1/34 (2006.01)
B01D 69/08 (2006.01)
B01D 63/04 (2006.01)

(52) U.S. Cl.
CPC .......... *A61M 1/1633* (2014.02); *B01D 2313/20* (2013.01); *B01D 69/084* (2013.01); *B01D 2319/02* (2013.01); *B01D 63/043* (2013.01); *A61M 1/3417* (2014.02); *A61M 1/16* (2013.01)
USPC ............ 210/321.79; 210/321.64; 210/321.71; 210/321.8; 210/321.81; 210/321.88; 210/321.9; 210/456; 210/647

(58) Field of Classification Search
USPC ............... 210/321.72, 321.6, 321.64, 321.79, 210/321.8, 321.81, 321.88, 321.89, 321.9, 210/456, 645, 646; 604/6.09, 6.04, 6.1, 604/6.11, 4.01, 5.01, 5.02, 5.03, 5.04
See application file for complete search history.

(56) References Cited

U.S. PATENT DOCUMENTS

| 4,227,295 A | 10/1980 | Bodnar et al. |
| 4,289,623 A | 9/1981 | Lee |

(Continued)

FOREIGN PATENT DOCUMENTS

| FR | 2581557 | * 11/1986 |
| JP | 61276563 A | 12/1986 |

(Continued)

OTHER PUBLICATIONS

English language machine translation of JP-2003-265597, pp. 1-18.*

(Continued)

*Primary Examiner* — David C Mellon
*Assistant Examiner* — Pranav Patel
(74) *Attorney, Agent, or Firm* — Browdy and Neimark, PLLC

(57) ABSTRACT

A dialyzer composed of: first and second dialyzation chambers, and an intermediate chamber interposed between the first and second dialyzation chambers. Each dialyzation chamber has opposed first and second ends and contains a filter member that separates the chamber into a blood compartment and a dialysate compartment. Each of the compartments extends between first and second ends. Each of the chambers has a respective one of a blood inlet or outlet and a dialysate inlet or outlet arranged so that blood and dialysate flow in counter-current to one another in both chambers. The intermediate chamber is connected to form a dialysate-free blood flow passage between the blood compartments.

16 Claims, 5 Drawing Sheets

(56) References Cited

U.S. PATENT DOCUMENTS

| | | | |
|---|---|---|---|
| 4,396,510 A | 8/1983 | Hsei | |
| 4,707,268 A | 11/1987 | Shah et al. | |
| 5,084,244 A | 1/1992 | Muramoto | |
| 5,700,372 A | 12/1997 | Takesawa et al. | |
| 6,315,895 B1 * | 11/2001 | Summerton et al. | 210/96.2 |
| 6,406,631 B1 | 6/2002 | Collins et al. | |
| 6,623,638 B2 | 9/2003 | Watkins et al. | |
| 6,843,779 B1 | 1/2005 | Andrysiak et al. | |
| 7,285,106 B2 * | 10/2007 | Collins et al. | 604/5.04 |
| 2003/0010702 A1 * | 1/2003 | Stillig et al. | 210/321.8 |
| 2004/0127842 A1 | 7/2004 | Collins et al. | |
| 2004/0200768 A1 | 10/2004 | Dannenmaier et al. | |
| 2008/0004712 A1 * | 1/2008 | Humes et al. | 623/23.65 |
| 2011/0139704 A1 | 6/2011 | Choi et al. | |

FOREIGN PATENT DOCUMENTS

| | | | |
|---|---|---|---|
| JP | 09276401 A | | 10/1997 |
| JP | 2003265597 | * | 9/2003 |
| JP | 2005118506 A | | 5/2005 |

OTHER PUBLICATIONS

English language machine translation of FR 2581557; pp. 1-2.*

* cited by examiner

DOUBLE FIBER BUNDLE DIALYZER

CROSS-REFERENCE TO RELATED APPLICATION

Applicant claims priority rights for Provisional Application No. 61/080,769, filed on Jul. 15, 2008, the disclosure of which is incorporated herein by reference.

STATEMENT REGARDING FEDERALLY SPONSORED RESEARCH OR DEVELOPMENT

This invention was made with government support under 5R42DK64500 awarded by National Institutes of Health (NIH), Bethesda, MD. The government has certain rights in the invention.

BACKGROUND OF THE INVENTION

The present invention relates to dialyzers, and particularly single-unit dialyzers that can be used with all existing dialysis equipment to provide dialytic therapies having increased efficiency.

BRIEF SUMMARY OF THE INVENTION

A dialyzer according to the invention is composed of two bundles of hollow fibers constituted by semi-permeable membranes, preferably housed within a single casing that delimits, in effect, two chambers. The dialyzer further includes an intermediate chamber in which blood flows from one fiber bundle to the other so that the blood coming from the first fiber bundle becomes intermixed and thus homogenized. This dialyzer is arranged to be connected to a standard dialysis machine via a blood inlet and outlet and a dialysate inlet and outlet. No additional connections are required.

DETAILED DESCRIPTION OF THE INVENTION

Figure 1:
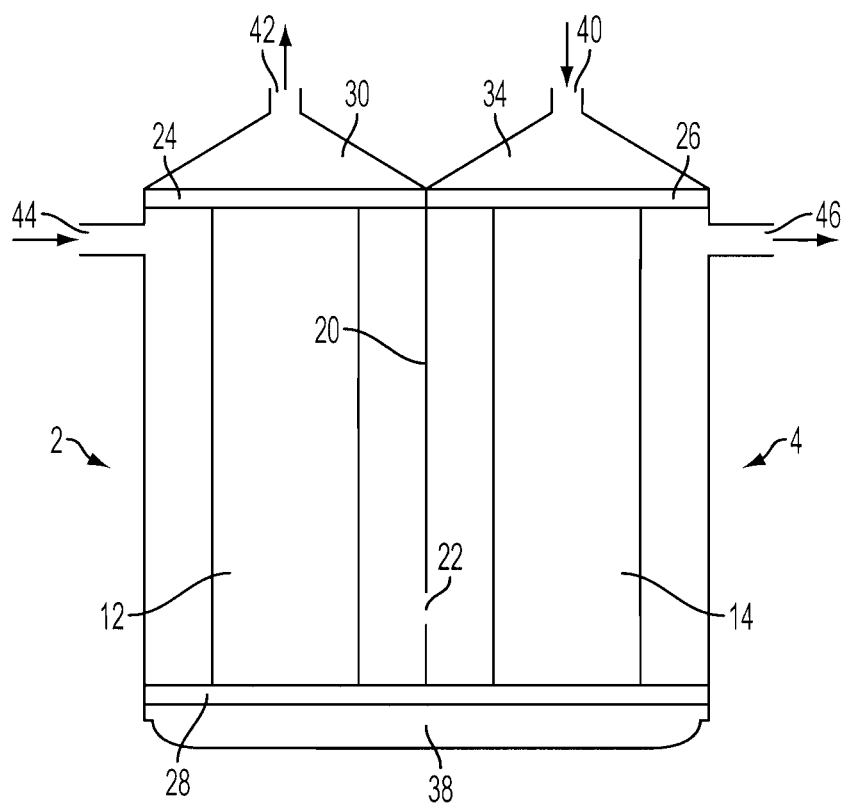
FIG. 1 is a simplified, elevational, pictorial view of one preferred embodiment of a dialyzer according to the invention.

FIG. 1 shows one preferred embodiment of the invention, which can be delineated as a double fiber bundle dialyzer. This apparatus is composed, in effect, of an outer casing that delimits two dialyzation chambers 2, 4 that may be disposed, effectively, side by side. Each dialyzation chamber 2, 4 is closed off by a respective part of the outer casing and manifolds 24, 26, 28, to be described below. Each dialyzation chamber contains a filter member in the form of a bundle 12, 14, respectively, of semi-permeable hollow membrane fibers. Each fiber has the form of a small diameter hollow tube. The outer casing parts have a common wall 20, the common wall being provided, near the bottom of the outer casing, with an opening 22 forming a constricted passage for dialysate.

Manifold 24 is provided with openings that place the upper ends of the fibers of bundle 12 in communication with a blood outlet compartment 30, while manifold 26 is provided with openings that place the upper ends of the fibers of bundle 14 in communication with a blood inlet compartment 34. Compartments 30 and 34 are delimited by header caps.

Manifold 28 is provided with openings that place the lower ends of the fibers of bundles 12 and 14 in communication with an intermediate chamber 38 in which blood flows from the fibers of bundle 14 to the fibers of bundle 12 while blood from the various fibers become intermixed so that the blood entering the fibers of bundle 12 is of a more uniform composition. The component delimiting chamber 38 may be a further header cap.

Manifolds 24, 26 and 28 close off the portions of each chamber 2, 4 through which dialysate flows so that dialysate cannot flow into chamber 38.

Figure 2:
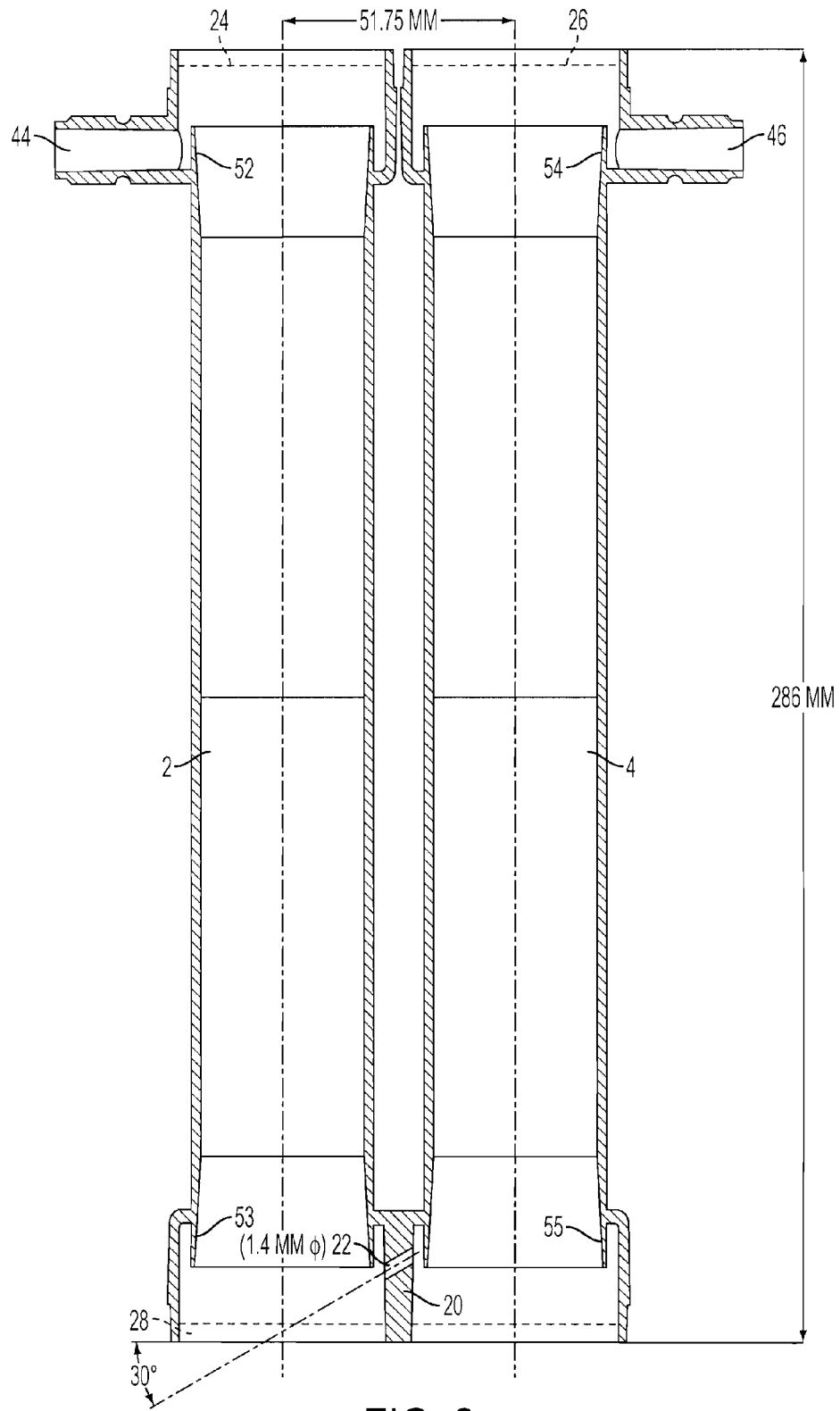
FIG. 2 is an elevational, cross-sectional view of the casing according to a preferred embodiment of the invention.

FIG. 2 is a cross-sectional view of one preferred embodiment of the outer casing of a dialyzer according to the present invention. This embodiment is composed essentially of two circularly cylindrical tubes delimiting the dialyzation chambers 2, 4. Common wall 20 with opening 22 is provided at the lower end of the outer casing. By way of example, opening 22 may have a circular cross section with a diameter of the order of 1.4 mm and a longitudinal axis that has a length of the order of 6.6 mm and is inclined at an angle of the order of 60°-85° to the longitudinal axis of each chamber 2, 4 and oriented to produce a flow having a direction with a component parallel to the direction of dialysate flow in chamber 4.

Also by way of example, the overall length of the outer casing may be of the order of 28.6 cm and the distance between the longitudinal axes of chambers 2 and 4 may be of the order of 5.2 cm.

The diameter of each chamber 2, 4 is of the order of 3.6 cm at the center of the chamber. However, other diameter values can be used. In general, the diameter of the chamber will be related to the size of the fiber bundle. As a rule of thumb, the total area of the fibers in a bundle, based on the outer diameters of all of the fiber OD in one plane, should preferably be approximately 50-55% of the cross-sectional area of the chamber in the same plane.

The locations of manifolds 24, 26 and 28 are shown in broken lines in FIG. 2.

Figure 3:
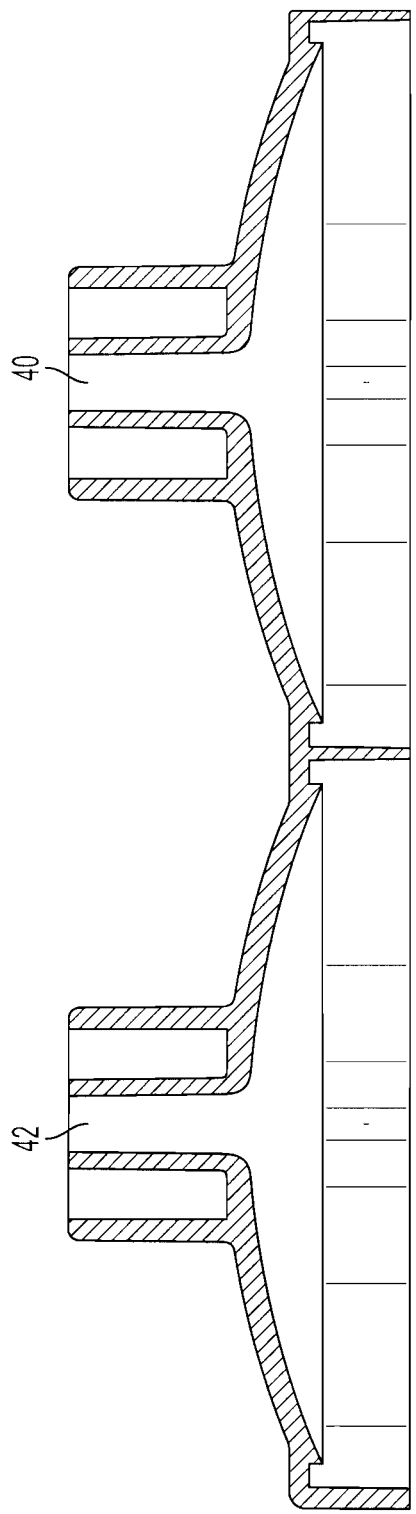
FIG. 3 is an elevational, cross-sectional view of top header caps of a dialyzer according to the invention.
Figure 4:
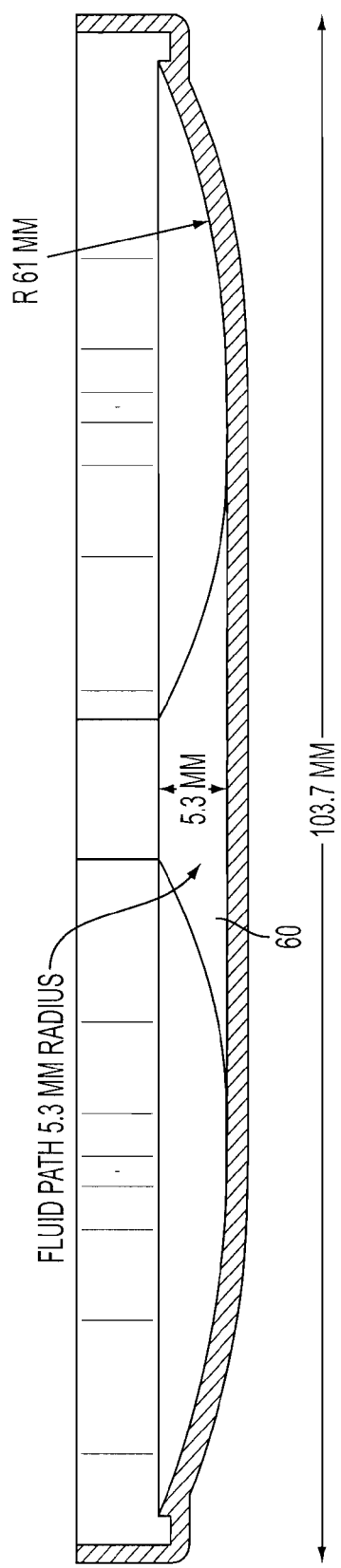
FIG. 4 is an elevational, cross-sectional view of a bottom header cap of a dialyzer according to the invention, viewed in the direction of cross-section line 4-4 in FIG. 5.
Figure 5:
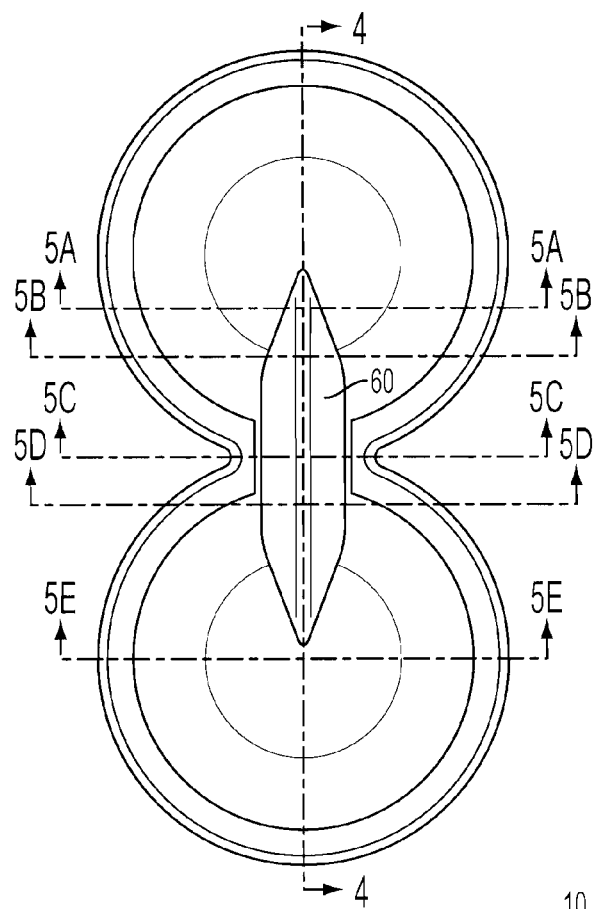
FIG. 5 is a top plan view of the header cap of FIG. 4.
Figure 5A:
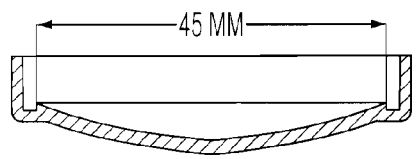
FIGS. 5A-5E are cross-sectional views viewed in the direction of cross-section lines 5A-5A, 5B-5B, 5C-5C, 5D-5D and 5E-5E, respectively, in FIG. 5
Figure 5C:
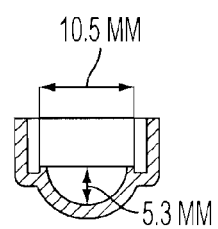
Figure 5D:
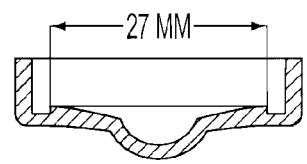
Figure 5B:
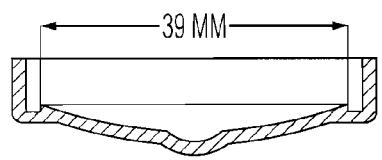
Figure 5E:
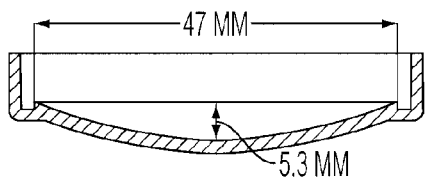

FIG. 3 shows an example of top header caps delimiting compartments 30 and 34.

FIGS. 4, 5 and 5A-5E show an example of the bottom header cap delimiting compartment 38.

Some exemplary dimensions are shown in FIGS. 2, 4 and 5A-5E.

The bottom header cap is provided with a channel 60 designed to aid blood flow from fiber bundle 14 to fiber bundle 12. The dimensions of channel 60 are of the order of 10.5 mm wide and 5.3 mm high and the radius of curvature of channel 60 is also 5.3 mm. Channel 60 extends essentially between the midpoints of the two halves of the header cap. This provides a path for the blood to travel and mix while minimizing the pressure drop where chamber 38 narrows between fiber bundles. The top part is curved but the bottom forms a semicircle or "D shape" with the flat top of the manifold.

The volumes enclosed by the fibers of bundles 12 and 14 define respective blood compartments in chambers 2 and 4, while the volumes surrounding the fibers of bundles 12 and 14 define respective dialysate compartments in chambers 2 and 4.

Manifolds 24 and 26 constitute walls that close off the upper ends of the dialysate compartments and manifold 28 constitutes a wall that close off the lower ends of the dialysate compartments. The lower end of common wall 20 bounds a constricted passage between the two dialysate compartments.

Compartment 34 is provided with an inlet passage 40 for the delivery of blood into the apparatus, while compartment 30 has a blood outlet 42 for removal of blood from the apparatus. In addition, chamber 2 is provided with a dialysate inlet 44, while chamber 4 is provided with a dialysate outlet 46.

During a dialysis procedure, fresh dialysate is introduced through inlet 44 into the dialysate compartment in chamber 2, flows through opening, or restricted passage, 22 near the bottom of common wall 20 into the dialysate compartment in chamber 4, and then out through outlet 46. At the same time, blood that is to be dialyzed is introduced into chamber 34 via inlet 40, flows through the fibers of bundle 14 into intermediate chamber 38, and then flows through the fibers of bundle 12 to chamber 30 and finally exits the apparatus through outlet 42.

In chamber 4, plasma water is removed from blood flowing through the fibers of bundle 14 and is transferred into the dialysate compartment in chamber 4 by being filtered across the semipermeable membranes forming the walls of the fibers of bundle 14.

Upon exiting the blood compartment in chamber 4, the blood enters and flows through intermediate chamber 38 and then into the blood compartment in chamber 2. The function of intermediate chamber 38 will be described below.

As the blood flows through the blood compartment in chamber 2, i.e., through the fibers of bundle 12, fresh dialysate is filtered from the dialysate compartment, across the semipermeable membranes forming the walls of the fibers of bundle 12 and into the blood compartment of chamber 2 at a rate substantially equal to the rate at which plasma water was filtered from the blood compartment of chamber 4. The manner in which the filtration rates are controlled will be described below.

Thus, ultrafiltration is performed in chamber 4, while substitution fluid is introduced from fresh dialysate into the blood compartment in chamber 2 via backfiltration. The dialyzer is thus capable of achieving a high rate of ultrafiltration with the introduction of substitution fluid by backfiltration that results in an on-line Hemodiafiltration (HDF) treatment. HDF is a hemodialysis modality that combines the use of dialysis fluid for the diffusive removal of toxins with larger volumes of ultrafiltration (compared to standard hemodialysis) to remove middle weight molecules by convection.

Fresh dialysate fluid for this system may be generated using existing methods and standard dialysis equipment. The dialysate fluid enters the dialysate compartment in chamber 2 and flows in counter-current with respect to the blood flow. This dialysate fluid performs two functions: 1) it acts to set up a concentration gradient relative to the blood compartment, thereby inducing diffusion of solutes across the semi-permeable membranes from the blood compartment to the dialysate compartment in chamber 2; and 2) because of the relatively higher pressure of the incoming dialysate compared to the blood compartment pressure, it produces a backfiltration of dialysate into the blood compartment.

Upon exiting chamber 2, the dialysate fluid enters the dialysate compartment in chamber 4, still flowing in counter-current with respect to the blood flow in the respective blood compartment. The dialysate flow rate increases as the dialysate flows through the dialysate compartment in chamber 4, due to filtration of plasma water from the blood compartment across the semi-permeable membranes of the fibers of bundle 14.

Dialysate also flows around the fibers of each fiber bundle, entering at one side of the respective dialysate chamber and flowing diagonally across the chamber and around the membrane fibers before exiting at the other side, and the other end, of the respective chamber. This flow across, or around, both fiber bundles may enhance fiber surface contact and diffusive removal of substances.

Upon exiting the dialyzer, the spent or used dialysate is transported back to the dialysis machine and to the drain in a conventional manner.

The fibers of both bundles may be of the same material and both bundles also have the purpose of diffusive removal of toxins. It is also possible, at high protein concentrations in the blood, that some backfiltration starts in fiber bundle 14.

The volumetric control of a dialysis machine ensures proper ultrafiltration and controls the rates of filtration and backfiltration. The fiber bundle involved in the backfiltration, in chamber 2, acts as a final fluid quality filter and has been shown to bring both bacteria and endotoxin to levels that approach pharmaceutical grade fluids.

The advantage of this system is that small molecules such as urea can be removed efficiently due to the appropriately large surface area of the two fiber bundles, and midsized molecules are removed efficiently due to the large filtration with backfiltration, which is optimized with this double fiber bundle configuration. No additional dialyzers, no final ultrafilters, no additional pumps or external equipment and no external substitution fluid are required.

The rate of filtration and backfiltration will be controlled by the resultant pressures due to the blood and dialysate flow rates. This is discussed in U.S. Pat. No. 6,406,631, issued Jun. 18, 2002, the disclosure of which is incorporated herein by reference.

There are several advantages to the proposed double fiber bundle dialyzer as compared with the prior art. First, the dialyzer according to the invention can be given a large membrane surface area that will result in improved urea and creatinine removal.

The largest dialyzer commercially available today has a membrane surface area of 2.5 $m^2$. Dialyzers employing known ultrafiltration technology would exhibit a tendency to clot if given a larger membrane surface area. In addition, if the filtration rate is too high in known dialyzers, an alarm indicating a reverse ultrafiltration error will be produced because the TMP (transmembrane pressure=average blood side pressure−average dialysate side pressure) becomes negative and implies fluid is fluxed across the membrane from the dialysate into the blood. In the past, when fluid quality was more questionable, this may have been a problem. Various dialysis machines measure TMP in different ways. Very few dialysis machines measure the blood in and blood out as well as the dialysate in and dialysate out pressures to get a true TMP. Most dialysis machines use the blood out and dialysate out pressures and an offset to calculate the TMP.

However, the novel technology on which the present invention is based makes possible a dialyzer having a membrane surface area of 3.0 $m^2$ or more. The double dialyzer configuration according to the present invention resolves the clotting issue as discussed herein, and also resolves the reverse ultrafiltration alarm problem by decreasing the dialysate out pressure due to the restricted passage between the dialysate compartments.

In addition, the rate of ultrafiltration and midsize molecule removal will be greater in the dialyzer according to the invention than in prior art systems having the same dialyzer area and similar Kuf, Kuf being the coefficient of ultrafiltration for the filter member, i.e., the rate of plasma water fluid flux across the membrane, or fiber wall, per hour per mmHg of transmembrane pressure (TMP). This is because the TMP is enhanced in the invention dialyzer by the two dialyzation chamber design.

Further, the dialysate distribution and resultant clearance will be better in dialyzers according to the invention, at least when crimped fibers are used for the membranes. Specifically, crimped fibers result in a more uniform dialysate flow throughout the dialyzer. This results in improved clearance of small molecules. Also, the provision of two separate dialysate compartments communicating via the restricted passage, or orifice, will help to redistribute the dialysate flows so any channeling, even with straight fibers, will be all but eliminated in the second dialysate compartment.

Moreover, the system according to the present invention is constructed and operated to maintain the counter-current dialysate flow throughout both bundles whereas at least one existing dialyzer has a single chamber with counter-current flow in one stage that contains a filter bundle and concurrent flow, i.e., blood and dialysate flows in the same direction, in a second stage containing another bundle, which greatly reduces the diffusion gradient. In the operation of that dialyzer, it is necessary to add substitution fluid directly into a space between the fiber bundles. If substitution fluid is not added, this dialyzer clots very quickly. The second stage will have a lower small molecule removal rate since the concentration gradient is smaller.

Furthermore, in prior art systems substitution fluid requires a separate filter for the fluid generated on-line and a separate pump to control infusion, making the system more complicated and expensive to run than a dialyzer according to the invention.

Specifically, dialyzers according to the invention are intended to be connected to standard dialysis machines that are already in dialysis clinics to perform an HDF treatment. To perform any of the other HDF treatments, prior art machines require a specialized structure that has extra sensors to measure the amount of filtration, separate pumps to return the substitution fluid and extra filters since they reinfuse the substitution fluid either directly into the blood line or into the header of the dialyzer. For example, these other systems will need to calculate the volume going into the system (blood and dialysate) and the volume coming out (blood and dialysate). The system needs to calculate the rates of filtration and then must add the proper amount of substitution fluid to the system to balance the fluid removed. So the equipment is complicated by balances or fluid control units that measure the fluid exchanged. This also requires a pump to infuse the substitution fluid directly into the blood line. Our system uses the existing fluid balancing system in the current machines. The fluid balancing system can be a diaphragm pump such as in the Frensius machines or flow meter controlled system such as in the Gambro machines.

An advantage of the present invention is that the double fiber bundle dialyzer can be used with any known dialysis machine with volumetric control to perform an HDF treatment without needing to set up additional infusion lines, filters and/or pumps or units.

Improved midsize molecule clearance is achieved in a dialyzer according to the invention by increasing filtration and backfiltration. More specifically, midsize molecules are removed more effectively by filtration (convection removal) and dialyzers according to the invention enhance convective removal by the action of the restricted dialysate passage 22 and by using the proper membranes.

Furthermore, a dialyzer according to the invention can be used in existing dialysis machines without the need for additional hardware or modifications.

For example, a dialyzer according to the invention can be used with known dialysis machines, such as a standard Fresenius machine, on which a dialyzer according to the invention was tested, in place of a conventional dialyzer, using the exact same set-up as for a standard dialysis treatment, including standard blood lines. The dialyzer according to the invention will automatically enhance the filtration and back filtration based on its design. Nearly all current dialysis machines have a place for an ultrafilter. This is a filter that filters the dialysate fluid prior to reaching the dialyzer. It is a component of a dialysis machine, possibly not needed in systems according to the present invention. An ultrafilter is usually a hollow fiber filter similar to a standard dialyzer, but is designed to have the fluid diffuse across the fibers (filtration) and then flow to the dialyzer. All machines marketed within the past 5 years or more have a built in ultrafilter (also called an endotoxin filter).

The double fiber bundle dialyzer according to the invention differs from the prior art (e.g., U.S. Pat. No. 5,700,372) in several ways. One important difference is that in the system according to the invention, blood passes through and exits the fibers of bundle 14, then enters a large space, i.e., intermediate chamber 38, where the blood exiting all of the fibers of bundle 14 is mixed together before entering the fibers of bundle 12. No filtration, or back filtration, or substitution of fluid occurs in intermediate chamber 38; only blood flows through intermediate chamber 38.

Chamber 38 performs an important function that serves to eliminate, or at least minimize, the adverse effects of a common problem in dialysis known as "channeling". Channeling can occur on the dialysate side or the blood side of the fibers. Channeling on the blood side is when blood flows through different fibers at different rates. In the fibers in which a relatively fast flow occurs, the fibers see more blood than do the fibers in which a slower blood flow occurs, although ultrafiltration occurs from all of the fibers. In the fibers experiencing slow blood flow, while plasma water is being removed by ultrafiltration (raising the hematocrit: the proportion of blood volume that is occupied by red blood cells), the blood will tend to clot and the fibers will become blocked. This results in more flow through the other fibers and a reduction in the active filter surface area, i.e., the filter surface area participating in the filtering of toxins. A reduction in the active filter surface area of the dialyzer will reduce the efficiency of the dialyzer and the treatment. At the same time, the reduction in the active filter surface area causes a higher pressure at blood inlet 40, which in turn causes more ultrafiltration in the remaining fibers. This higher ultrafiltration will lead to more clotting.

Since systems according to the invention have two smaller bundles of fibers separated by intermediate chamber 38, as the blood goes through the fibers of bundle 14 it becomes more concentrated (because of ultrafiltration). However, all of the blood exiting the fibers of bundle 14 enters the common intermediate chamber 38 and mixes together. This will include the blood that flowed slowly through one or more fibers and the blood that flowed faster through other fibers. The blood entering the fibers of bundle 12 will, therefore, be more homogenous. The pressure of the blood entering the fibers of bundle 12 will also be the same at all of the fiber walls, leading to a more consistent backfiltration and reconstitution of the blood returning to the body at nearly the same hematocrit at which it was pumped out of the body.

To summarize, intermediate chamber space 38 in the double fiber bundle system according to the invention acts to mix the blood while no filtration, or back filtration, or substitution of fluid is occurring so that the blood entering the fibers of bundle 12 is homogenous and at nearly the same pressure from one fiber to another.

An exemplary preferred embodiment of the invention may have the following specific parameters:

Dimensions of each fiber: ID=180-200 μm; wall thickness=filter member 35-50 μm; OD=250-300 μm; length=28 cm±3 cm;

Effective surface area of each fiber bundle=1.5 m²;

Number of fibers in each chamber, i.e., in each bundle=approximately 9500 fibers+/−500 fibers, the exact number depending on the diameter and length of the fibers.

The pore size for toxin removal should be selected to produce as sharp a drop as possible in the elimination rate of molecules at 65,000 or 66,000 Daltons (the universal mass unit or atomic mass unit). Little or no molecular weight substances above 65,000 or 66,000 Daltons should be removed. This will minimize protein losses during treatment.

One nonlimiting example of the membrane material of the fibers in bundles 12 and 14 would be a product marketed by Asahi Kasei Kuraray Medical Co., Ltd. under the trade names REXBRANE and Polysulfone APS, a polysulfone membrane with a hydrophilic gel layer.

The fibers should be crimped to enhance dialysate flow. This crimping gives the fibers a form that follows a sinuous path along their length, which is the form of the REXBRANE fibers.

Each fiber bundle may have a KuF (Coefficient of Ultrafiltration) of 20-26 ml/h/(mmHg TMP), TMP can be calculated as the average pressure on the blood side of the membrane minus the average pressure on the dialysate side of the membrane. TMP is mostly determined by the hydrostatic pressure of the blood flow on the blood side of the membrane (favoring flux from the blood side to the dialysate side), the opposite pressure of the dialysate fluid on the dialysate side of the membrane (favoring dialysate fluid flux to the blood side) as well as the opposite pressure associated with the oncotic pressures (which is a form of osmotic pressure exerted by proteins in blood plasma that normally tends to pull water into the circulatory system) of the blood proteins (favoring fluid flux from the dialysate side to the blood side). As more fluid flows across a membrane from the blood side to the dialysate side, the oncotic pressures increase as the protein concentration increases due to less plasma water and a relatively higher protein concentration.

The true calculation of Kuf, therefore, can vary as a function of the protein concentrations, dialysate flows, and blood flows. The Kuf range given above was consistent for the specific embodiment tested using the Fresenius 2008 series dialysis machine and the blood and dialysate flows tested blood flow=350-550 ml/min and dialysate flow=800 ml/min). When the dialysate flow (Qd) is reduced to 500 ml/min, there is a drop in TMP (machine measured) of close to 100 mmHg. This is due to the increase in average dialysate side pressures. The incoming dialysate pressures are nearly the same at 800 and 500 ml/min dialysate flows, the pressures being approximately 200 mmHg±dependent on blood flow.

The pressure drop between the inlet and outlet of the dialysate compartment in chamber 2 is slight due to the presence of the constricted passage between the dialysate compartments. The pressure drop across the constricted passage is lower with a 500 ml/min flow rate since the flow is lower. This yields a higher average pressure in the dialysate compartment of chamber 4 for a 500 ml/min dialysate flow than for an 800 ml/min flow. The higher pressure on the dialysate side of chamber 4 yields a drop in TMP.

Also, the conventional volumetric controller (not shown) of the dialysis machine to which the dialyzer is connected, which makes sure that the dialysate volume entering via inlet 44 is the same as the volume that leaves via outlet 46, can apply a slight negative pressure at outlet 46, thereby pulling fluid from the blood side to make the incoming and outgoing volumes the same. Additional fluid removal is normally programmed into the dialysis machine in order to remove the excess fluid a patient consumes between treatments. This excess fluid removal is controlled by a separate pump in all dialysis machines and works in conjunction with the present invention.

The Kuf (coefficient of ultrafiltration) is calculated for the fibers of bundle 14 only using human blood reconstituted with saline and bovine albumin at a concentration of ~6 g/dL (this also effects the measured Kuf. If it was measured with saline, the Kuf would be calculated to be much higher due to the lower viscosity and lack of blood proteins, i.e. albumin).

In chamber 2, the dialysate compartment pressure drop with Qd=800 ml/min (dialyzer with incoming dialysate from the associated machine and provided with the restricted passage beneath common wall 20 as well as back filtration) =about 15 mmHg (this is a slight pressure drop due to the constricted passage at the outlet of the dialysate compartment in chamber 2).

In chamber 4, the pressure drop across the dialysate compartment with Qd=800 ml/min (with a large filtration volume from blood to dialysate side, the machine volume controller can cause a negative pressure at the outlet 46)=about 55 mmHg, with or without negative pressure at outlet 46, downstream of the restricted passage to outlet 46 (dialysate flows in counter-current to blood flow).

Constricted passage 22 in common wall 20 between the dialysate compartments in chambers 2 and 4 should preferably provide a pressure drop of ~100 mmHg with a Qd=800 ml/min, or a 50 mmHg drop with Qd=500 ml/min.

The total dialysate pressure drop between inlet 44 and outlet 46 should be about 170 mmHg. There is some variability dependent on blood flow, rate of filtration with backfiltration and access needle size used or catheter type (which effects venous pressure of returning blood at outlet 42).

The blood side pressure drop is dependent on blood flow and the size of the venous needle used to return the blood to the patient's body (using a smaller venous needle will result in a higher pressure leaving chamber 2), but can be approximated, for chamber 4, as a pressure drop, between chambers 34 and 38, of 40% of the pressure entering the dialyzer fibers (header pressure, chamber 34). For example, if the incoming pressure is 402 mmHg and the outgoing is 240 mmHg this is a difference of 162 mmHg, or 40% (=162/402), and approximately a 65% pressure drop of the pressure in chamber 38 to the exit chamber 30 (pressure drop across Chamber 2). The pressure drop in Chamber 2 will vary dependent on blood flow, a higher blood flow resulting in a higher pressure drop. In the operation of a dialyzer according to the invention, a pressure drop of 75% at blood flows of 550 ml/min and a pressure drop of 62% at blood flows of 350 ml/min were measured.

The double dialyzer according to the invention has two separate bundles of fibers for filtration, with fiber bundle headers at the ends of the chambers. Manifolds 24, 26 and 28 may be constituted by potting compound bodies. U.S. Pat. Nos. 4,227,295 (Bodnar) and 5,700,372 (Takesawa), the disclosures of which are incorporated herein by reference, describe common methods to manufacture dialyzers using the potting compound to form manifolds. This method can be used in the fabrication of a dialyzer according to the present invention. The fibers enter and exit through these bodies so that the blood encounters some resistance upon entering the fibers and the resistance at the entry to each fiber bundle aids filtration.

The potting compound is used to separate the internal pathways presented by the fibers from the dialysate compartments. This is done by inserting the fiber bundles into the dialyzer casing. Thus, a lower end header cap will be provided. The potting compound bodies are formed in place before the top and bottom header caps are put in place. To form the potting compound bodies, a special cap is clamped on each end of the casing and potting compound (polyurethane material) is injected into the special caps and around the fibers. The chambers are usually spun in order to distribute the potting compound so as to reliably form seals between the dialysate side and blood side of each chamber. Since blood flowing out of the fibers of bundle 14 will flow through chamber 38 and into the fibers of bundle 12, potting compound seals will be formed around the fiber ends that will extend into chamber 38, as well as around the fiber ends that will extend into compartments 30 and 34, after which the fiber bundle ends projecting from the potting compound bodies may be sliced off. The header caps may then be assembled to the ends of the casing.

Two separate dialysate compartments are provided in order to be able to provide the flow constriction 22 therebetween to control the rates of filtration and backfiltration. In fact, the flow constriction between dialysate compartments, near the bottom of wall 20, is a key component of the double dialyzer according to the invention. If the flow constriction yields too low of a pressure drop, the machine will alarm for low TMP because the average dialysate pressure will be too low for the amount of filtration the system produces. If the pressure drop across the flow constriction is too high (too small of a passage cross section), the dialyzer could clot as the TMP of fiber bundle 14 in chamber 4 increases (because of very low dialysate pressures), causing additional ultrafiltration of plasma water and hemoconcentrating the blood in chamber 4.

By having two separate bundles of fibers for blood and dialysate, it becomes possible to maintain a counter-current flow between dialysate and blood through the entire double dialyzer system, maximizing diffusive removal of blood toxins. The parameters presented herein have been found to produce good results. However, variations are possible within the framework of the invention. For example, the membrane fibers can have a smaller ID, and/or thinner walls, and/or smaller or larger fiber membrane surface areas (e.g., 0.9 to 1.8 $m^2$ for each bundle). It is possible to have a difference in area between the two fiber bundles. This could be, for example 1.3 $m^2$ for bundle 12 and 1.5 m2 for bundle 14, although this may make manufacturing more difficult. Unequal surface areas may also have to be balanced by possibly changing the filtration capability of the fiber bundles. If a fiber bundle having a smaller surface area were provided in one chamber, this may need to be compensated with a higher filtration capability in order to provide the correct filtration and backfiltration. If the inner diameter of each fiber were made smaller, the result would be an increase in pressure drop and an increase in filtration. There are numerous possible configurations.

Other variations, such as lower Kuf of the fiber bundles with higher pressure drops of the inter-dialysate chamber constriction are also possible, as well as higher Kuf and lower pressure drops. However, such variations should be within a small range to reach the optimal 25% of blood flow filtration. For example, a Kuf of 10 with a blood flow of 500 ml/min would require a TMP of 750 mmHg; however the limit for TMPs for the membranes is usually around 500 mmHg or they could break. Similarly, a Kuf of 30 requires a maximum TMP of 250 mmHg; however at a 500 ml/min blood flow rate, the minimum TMP achievable is about 300 mmHg. The TMP referred to is the actual measured TMP at the inlet and outlet of both blood side and dialysate side, not the machine calculated TMP.

The constricted passage 22 in wall 20 is important because if there were no constriction, the pressure at dialysate outlet 46 would be substantially equal to the pressure at dialysate inlet 44, so that there would be less filtration with backfiltration. Therefore, clearance of middle weight toxins would be reduced and there would also be problems with the dialysis machine because the dialysate pressure at outlet 46 would be higher than if the constricted passage was present. This higher pressure at outlet 46 will result in a reverse TMP alarm.

Also, a double fiber bundle with similar parameters but smaller total membrane surface areas (0.3 to 0.9 $m^2$ for each bundle) can be used to provide a hemodiafiltration treatment at lower blood flows (200 ml/min) and lower dialysate flows (100-500 ml/min). The constricted passage between dialysate compartments will still be required in order to drop the average of the dialysate side pressures to allow the double fiber bundle dialyzer system to run on standard equipment.

Distribution rings, or dialysate diverters, commonly used in this art, may also be provided near the inlet and outlet of dialysate ports 44 and 46, below manifolds 24 and 26, and at the bottom of the chambers, above manifold 28, to aid in distribution of the dialysate around the fibers. Examples of such diverters are disclosed in U.S. Pat. Nos. 4,396,510; 5,084,244; and 6,623,638, the disclosures of which are incorporated herein by reference.

The casing shown in FIG. 2 is provided with diverters 52, 53, 54 and 55, which may be integral parts of the casing. Dialysate entering via inlet 44 flows around diverter 52 and upwardly over the upper edge of diverter 52 before entering the dialysate compartment in chamber 2. Similarly, dialysate exiting from passage 22 will flow around diverter 55 and then under the lower edge of diverter 55 before entering the dialysate compartment in chamber 4. Diverters 53 and 54 are also used to aid in dialysate flow distribution by forcing the fluid to flow from the center of the dialyzer over the diverter to the periphery where dialysate will flow through restricted passage via diverter 53 and to port 46 via diverter 54. Since channeling commonly occurs along the walls of the chambers, the diverters force the dialysate away from the walls to the center where the fibers are located.

This present invention may also be used with the specialized dialysis machines capable of delivering HDF treatments. The use of pre-dilution HDF (fluid infused before entering the dialyzer) using the present invention as the dialyzer will deliver a rate of filtration equal to or greater than the amount of filtration of which a standard HDF dialyzer in the same pre-dilution modality is capable.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A dialyzer comprising:
first and second circularly cylindrical dialyzation chambers, and an intermediate chamber interposed between said first and second dialyzation chambers, wherein,
each of said dialyzation chambers has opposed first and second ends;
said dialyzation chambers are disposed side by side;
each of said dialyzation chambers contains a filter member that separates said dialyzation chamber into a blood compartment and a dialysate compartment, each of said compartments extending between said first and second ends;
said filter member in said first chamber is made of a filter material for filtering out plasma water from blood;
said filter member in said second dialyzation chamber is made of a filter material for passing dialysate from said dialysate compartment to said blood compartment;
said first dialyzation chamber has, at said first end thereof, a blood inlet communicating with said blood compartment and a dialysate outlet communicating with said dialysate compartment;
said second dialyzation chamber has, at said first end thereof, a blood outlet communicating with said blood compartment and a dialysate inlet communicating with said dialysate compartment;
said intermediate chamber extends between said second end of said first dialyzation chamber and said second end of said second dialyzation chamber and communicates only with said blood compartments during operation of said dialyzer to perform blood dialysis;
said blood and dialysate inlets and outlets are located to produce dialysate flows in counter-current to blood flows in both of said dialyzation chambers; and
said first and second dialyzation chambers are constructed to provide a dialysate flow path between said dialysate compartments at said second ends of said chambers, said dialysate flow path forming a constricted passage for dialysate that produces a dialysate pressure drop between said second dialyzation chamber and said first dialyzation chamber, wherein, for performing dialysis, the only connections to said dialyzer consist of said blood inlet, said blood outlet, said dialysate inlet and said dialysate outlet; and
wherein blood has a direction of flow in each of said blood compartments and said constricted passage is oriented to provide a flow path that forms and acute angle with the direction of blood flow in each of said blood compartments.

2. The dialyzer of claim 1, wherein said first and second dialyzation chambers are separated by a common wall having an opening that constitutes said dialysate flow path and provides said constricted passage between said dialysate compartments.

3. The dialyzer of claim 2, wherein said common wall has a portion located between said opening and said second ends of said dialyzation chambers.

4. The dialyzer of claim 3, wherein each of said filter members comprises a bundle of hollow fibers of the respective filter material.

5. The dialyzer of claim 1, wherein said constricted passage has a diameter of the order of 1.0 mm to 1.6 mm.

6. The dialyzer of claim 5, wherein said constricted passage has a circular cross section.

7. The dialyzer of claim 1, wherein said dialysate flow path is dimensioned to produce a dialysate pressure drop of 50 mmHg at a dialysate flow rate of 500 ml/min.

8. The dialyzer of claim 1, wherein said dialysate flow path is dimensioned to produce a dialysate pressure drop of approximately 100 mmHg at a dialysate flow rate of 800 ml/min.

9. The dialyzer of claim 1, wherein said dialysate flow path is dimensioned to produce a dialysate pressure drop of 50 mmHg at a dialysate flow rate of 500 ml/min and a dialysate pressure drop of approximately 100 mmHg at a dialysate flow rate of 800 ml/min.

10. The dialyzer of claim 1, wherein each said filter member is composed of a fiber bundle having a coefficient of ultrafiltration (Kuf) of 20-26 ml/h/(mmHg transmembrane pressure).

11. The dialyzer of claim 1, wherein, said constricted passage is dimensioned such that, during operation of said dialyzer, the dialysate pressure drop between said second dialyzation chamber and said first dialyzation chamber causes plasma water to be removed from blood in said blood compartment of said first dialyzation chamber and causes dialysate to be filtered from said dialysate compartment into said blood compartment of said second dialyzation chamber.

12. The dialyzer of claim 1, wherein blood flow in said first dialyzation chamber is in a direction opposite to the blood flow direction in said second dialyzation chamber, and said dialyzer is mounted, connected and oriented in operation so that blood flows in an upward direction in said second dialyzation chamber.

13. A dialyzer comprising:
first and second dialyzation chambers, and an intermediate chamber interposed between said first and second dialyzation chambers, wherein,
each of said dialyzation chambers has opposed first and second ends;
each of said dialyzation chambers contains a filter member that separates said dialyzation chamber into a blood compartment and a dialysate compartment, each of said compartments extending between said first and second ends;
said filter member in said first chamber is made of a filter material for filtering out plasma water from blood;
said filter member in said second dialyzation chamber is made of a filter material for passing dialysate from said dialysate compartment to said blood compartment;
said first dialyzation chamber has, at said first end thereof, a blood inlet communicating with said blood compartment and a dialysate outlet communicating with said dialysate compartment;
said second dialyzation chamber has, at said first end thereof, a blood outlet communicating with said blood compartment and a dialysate inlet communicating with said dialysate compartment;
said intermediate chamber extends between said second end of said first dialyzation chamber and said second end of said second dialyzation chamber and communicates only with said blood compartments during operation of said dialyzer to perform blood dialysis;
said blood and dialysate inlets and outlets are located to produce dialysate flows in counter-current to blood flows in both of said dialyzation chambers, wherein
said first and second dialyzation chambers are constructed to provide a dialysate flow path between said dialysate compartments at said second ends of said chambers, said dialysate flow path forming a constricted passage for dialysate that produces a dialysate pressure drop between said second dialyzation chamber and said first dialyzation chamber, wherein, for performing dialysis, the only connections to said dialyzer consist of said blood inlet, said blood outlet, said dialysate inlet and said dialysate outlet, and said dialyzer further comprises a first flow diverter positioned between said constricted passage and said dialysate compartment at said second end of first dialyzation chamber for distributing dialysate exiting said constricted passage around said hollow fibers in said first dialyzation chamber; and wherein each of said dialyzation chambers has a longitudinal axis and said dialysate flow path extends in a direction that is inclined at an acute angle with the longitudinal axis of at least said second dialyzation chamber.

14. The dialyzer of claim 13, wherein said dialysate flow path is oriented to produce a dialysate flow in a direction that intersects said first flow diverter.

15. The dialyzer of claim 13, wherein the acute angle has a value of the order of 60° to 85°.

16. The dialyzer of claim 13, further comprising a second flow diverter surrounding said dialysate compartment at said first end of said dialysate compartment in said second dialyzation chamber for distributing dialysate from said dialysate inlet around said hollow fibers in said second dialyzation chamber.

* * * * *